US005597800A

United States Patent [19]
Eibl et al.

[11] Patent Number: 5,597,800
[45] Date of Patent: *Jan. 28, 1997

[54] TREATMENT WITH LYS-PLASMINOGEN OF REPERFUSION INJURY AND BRAIN EDEMA CAUSED BY ISCHEMIA

[75] Inventors: Johann Eibl; Ludwig Pichler; Hans-Peter Schwarz, all of Vienna, Austria

[73] Assignee: Immuno Aktiengesellschaft, Vienna, Austria

[ * ] Notice: The term of this patent shall not extend beyond the expiration date of Pat. No. 5,520,912.

[21] Appl. No.: 345,468

[22] Filed: Nov. 21, 1994

Related U.S. Application Data

[63] Continuation of Ser. No. 88,033, Jul. 2, 1993, abandoned.
[51] Int. Cl.$^6$ .......................... A61K 38/48; A61K 38/00
[52] U.S. Cl. .......................... 514/12; 424/94.64; 514/802
[58] Field of Search .......................... 424/94.64; 514/12, 514/802

[56] References Cited

U.S. PATENT DOCUMENTS

| | | | |
|---|---|---|---|
| 4,808,405 | 2/1989 | Smith et al. | 424/94.3 |
| 4,996,050 | 2/1991 | Tsukada et al. | 424/94.2 |
| 5,084,274 | 1/1992 | Griffin et al. | 424/94.64 |
| 5,256,642 | 10/1993 | Fearon et al. | 514/8 |

OTHER PUBLICATIONS

Fredenburgh et al., J. of Bio. Chem., vol. 207:26150–26156 (Dec. 1992).
Shih et al., P.S.F.B.M. vol. 202:258–264 (1993).
Nieuwenhuizen et al., Eur. J. Biochem., vol. 174:163–169 (1988).
Saragovi et al., Science, vol. 253:792–795 (Aug. 1991).
Schalij et al., Neth. J. Med., 40:69–75 (Feb. 1992).
Pacouret et al., Arch. Mal. Coeur Vaiss, 83:25–29 (Feb. 1990).
Juhan et al., Bull Acad. Natl. Med., 174:197–207 (Feb. 1990).
Giraud et al., J Mal Vasc, 10:321–326 (1985).
Kerrigan et al., Microsurgery, vol. 14:165–175 (1993).
Werner et al., Stroke, vol. 22:910–914 (Jul. 1991).
Braunwald et al., J. Clin. Invest., vol. 76:1713–1719 (Nov. 1985).
Wauquier et al., Neuropharmacology, vol. 28:837–846 (1989).
Oh et al., Stroke, vol. 22:915–921 (Jul. 1991).

*Primary Examiner*—David M. Naff
*Assistant Examiner*—S. Saucier
*Attorney, Agent, or Firm*—Foley & Lardner

[57] ABSTRACT

A treatment of ischemia and the attendant reperfusion injury entails the administration plasmin and plasmin-forming proteins, including lys-plasminogen and similar substances. Lys-plasminogen, which can be obtained from the proteolytic cleavage of glu-plasminogen, has been found to have a protective effect on tissue that has been injured by ischemic conditions. The administration of lys-plasminogen alone, in a dosage of about 10–1000 caseinolytic units/kg, can be used to treat subjects during the time of reperfusion and after reperfusion has already occurred. Lys-plasminogen also can be administered in conjunction with clot lysis therapies, such as those that employ tissue plasminogen activator and the like. Lys-plasminogen can also lessen cerebral edema which results from cerebral ischemia.

9 Claims, 4 Drawing Sheets

FIG. 1

|  | Description | Score |
|---|---|---|
| State of consciousness: | normal | 0 |
|  | restless | 1 |
|  | apathetic | 2 |
|  | dazed | 3 |
|  | seizures | 4 |
| Gait: | normal | 0 |
|  | tensed paws | 1 |
|  | turning | 2 |
|  | hypomotility | 3 |
|  | unable to stand | 4 |
| Overhead ladder (45°): | climbs up | 0 |
|  | hangs for 5 seconds and raises hind legs | 1 |
|  | hangs for five seconds | 2 |
|  | hangs < 5 seconds | 3 |
|  | no grasp reflex | 4 |
| Vertical, rotating disk: | withstands rotation of 180° for > 5 seconds | 0 |
|  | withstands rotation of 180° for < 5 seconds | 1 |
|  | holds on only up to 90° | 2 |
|  | cannot hold on at all | 3 |
| Muscle tonus: | normal | 0 |
|  | weak | 1 |
| Total score: |  | 16 |
| Death (except due to operation) |  | 18 |

FIG. 2

| Substance Dose/kg | Administration schedule | Procedure (n animals) | Results |
|---|---|---|---|
| Lys-plasminogen 200 CU | With blood reperfusion | Edema (3 groups, n = 9 or 10 animals each) | Trend toward protective effect, not significant* |
| Lys-plasminogen 250 CU | 15 min before beginning of ischemia | Edema (3 groups, n = 15 or 17 each) | No effect |
| Lys-plasminogen 500 CU | 250 CU before beginning of ischemia +250 CU with blood reperfusion | Edema (3 groups, n = 1.5 each) | Significant protective effect |
| Buffer | Before beginning of ischemia with blood reperfusion | Edema (3 groups, n = 6 each) | No effect |
| Lys-plasminogen 500 CU | With blood reperfusion | Edema (3 groups, n = 6 each) | Significant protective effect (see Fig. 3) |
| Buffer | With blood reperfusion | Edema (3 groups, n = 7 or 8 each) | No effect (see Fig. 4) |
| Lys-plasminogen 500 CU | With blood reperfusion | Neurologic deficits (3 groups, n = 10 each) | Significant protective effect (see Fig. 5) |
| Buffer | With blood reperfusion | Neurologic deficits (3 groups, n = 6 each) | No effect (see Fig. 6) |
| Lys-plasminogen 500 CU | 30 min after blood reperfusion | Edema (3 groups, n = 8 or 9 each) | Significant protective effect |
| Lys-plasminogen 500 CU | 60 min after blood reperfusion | Edema (3 groups, n = 5 or 6 each) | No effect |

TREATMENT WITH LYS-PLASMINOGEN OF REPERFUSION INJURY AND BRAIN EDEMA CAUSED BY ISCHEMIA

This application is a continuation of U.S. application Ser. No. 08/088,033, filed Jul. 2, 1993, now abandoned.

BACKGROUND OF THE INVENTION

Stroke remains the third most common cause of death in the industrial world, ranking behind ischemic heart disease and cancer. Strokes are responsible for about 300,000 deaths annually in the United States and about 11,000 deaths annually in Austria. Strokes are also a leading cause of hospital admissions and long-term disabilities. Accordingly, the socioeconomic impact of stroke and its attendant burden on society is practically immeasurable.

"Stroke" is defined by the World Health Organization as a rapidly developing clinical sign of focal or global disturbance of cerebral function with symptoms lasting at least 24 hours. Strokes are also implicated in deaths where there is no apparent cause other than an effect of vascular origin.

Strokes are typically caused by blockages or occlusions of the blood vessels to the brain or within the brain. With complete occlusion, arrest of cerebral circulation causes cessation of neuronal electrical activity within seconds. Within a few minutes after the deterioration of the energy state and ion homeostasis, depletion of high energy phosphates, membrane ion pump failure, efflux of cellular potassium, influx of sodium chloride and water, and membrane depolarization occur. If the occlusion persists for more than five to ten minutes, irreversible damage results. With incomplete ischemia, however, the outcome is difficult to evaluate and depends largely on residual perfusion and the availability of oxygen. After a thrombotic occlusion of a cerebral vessel, ischemia is rarely total. Some residual perfusion usually persists in the ischemic area, depending on collateral blood flow and local perfusion pressure.

Cerebral blood flow can compensate for drops in mean arterial blood pressure from 90 to 60 mm Hg by autoregulation. This phenomenon involves dilatation of downstream resistant vessels. Below the lower level of autoregulation (about 60 mm Hg), vasodilatation is inadequate and the cerebral blood flow falls. The brain, however, has perfusion reserves that can compensate for the fall in cerebral blood fall. This reserve exists because under normal conditions only about 35% of the oxygen delivered by the blood is extracted. Therefore, increased oxygen extraction can take place, provided that normoxia and normocapnea exist. When distal blood pressure falls below approximately 30 mm Hg, the two compensatory mechanisms (autoregulation and perfusion reserve) are inadequate to prevent failure of oxygen delivery.

As flow drops below the ischemic threshold of 23 ml/100 g/minute, symptoms of tissue hypoxia develop. Severe ischemia may be lethal. When the ischemia is moderate, it will result in "penumbra." In the neurological context, penumbra refers to a zone of brain tissue with moderate ischemia and paralyzed neuronal function, which is reversible with restoration of adequate perfusion. The penumbra forms a zone of collaterally perfused tissue surrounding a core of severe ischemia in which an infarct has developed. In other words, the penumbra is the tissue area that can be saved, and is essentially in a state between life and death.

When a clot is degraded and the blood flow to the penumbra is restored, a phenomenon known as reperfusion injury can occur. Portions of the injured tissue in the penumbra can be killed or further injured by the re-entry of oxygen or other substances into the area affected by the ischemia. In view of this phenomenon, the extent of tissue damage resulting from ischemia is determined both by the time required to achieve opening of an occluded vessel and by the series of reactions that follow as a result of reperfusion and the re-entry of oxygen to the affected tissue.

Although an ischemic event can occur anywhere in the vascular system, the carotid artery bifurcation and the origin of the internal carotid artery are the most frequent sites for thrombotic occlusions of cerebral blood vessels, which result in cerebral ischemia. The symptoms of reduced blood flow due to stenosis or thrombosis are similar to those caused by middle cerebral artery disease. Flow through the ophthalmic artery is often affected sufficiently to produce amaurosis fugax or transient monocular blindness. Severe bilateral internal carotid artery stenosis may result in cerebral hemispheric hypoperfusion. This manifests with acute headache ipsilateral to the acutely ischemic hemisphere. Occlusions or decrease of the blood flow with resulting ischemia of one anterior cerebral artery distal to the anterior communicating artery produces motor and cortical sensory symptoms in the contralateral leg and, less often, proximal arm. Other manifestations of occlusions or underperfusion of the anterior cerebral artery include gait ataxia and sometimes urinary incontinence due to damage to the parasagittal frontal lobe. Language disturbances manifested as decrease spontaneous speech may accompany generalized depression of psychomotor activity.

Most ischemic strokes involve portions or all of the territory of the middle cerebral artery with emboli from the heart or extracranial carotid arteries accounting for most cases. Emboli may occlude the main stem of the middle cerebral artery, but more frequently produce distal occlusion of either the superior or the inferior branch. Occlusions of the superior branch cause weakness and sensory loss that are greatest in the face and arm. Occlusions of the posterior cerebral artery distal to its penetrating branches cause complete contralateral loss of vision. Difficulty in reading (dyslexia) and in performing calculations (dyscalculia) may follow ischemia of the dominant posterior cerebral artery. Proximal occlusion of the posterior cerebral artery causes ischemia of the branches penetrating to calamic and limbic structures. The clinical results are hemisensory disturbances that may chronically change to intractable pain of the defective site (thalamic pain).

A significant event in cerebral ischemia is known as the transient ischemic attack ("TIA"). A TIA is defined as a neurologic deficit with a duration of less than 24 hours. The TIA is an important sign of a ischemic development that may lead to cerebral infarction. Presently, no ideal treatment for TIA exists, and there are no generally accepted guidelines as to whether medical or surgical procedures should be carried out in order to reduce the incidence of stroke in subjects with TIA.

The etiology of TIA involves hemodynamic events and thromboembolic mechanisms. Because most TIAs resolve within one hour, a deficit that lasts longer is often classified as presumptive stroke and is, accordingly, associated with permanent brain injury. Therefore, computed tomographic brain scans are used to search for cerebral infarction in areas affected by TIAs lasting longer than several hours. In sum, the relevant clinical distinction between a TIA and a stroke is whether the ischemia has caused brain damage, which is typically classified as infarction or ischemic necrosis. Subjects with deteriorating clinical signs might have stroke in evolution or are classified as having progressive stroke. In this clinical setting, clot propagation is possibly an important factor in disease progression.

There are a myriad of other diseases caused by or associated with ischemia. Vertebrobasilar ischemia is the result of the occlusion of the vertebral artery. Occlusion of the vertebral artery and interference with flow through the ipsilateral posterior inferior cerebellar artery causes lateral medullary syndrome, which has a symptomology including vertigo, nausea, vomiting nystagmus, ipsilateral ataxia and ipsilateral Herner's syndrome. Vertebrobasilar ischemia often produces multifocal lesions scattered on both sides of the brain stem along a considerable length. Except for cerebellar infarction and the lateral medullary syndrome, the clinical syndromes of discrete lesions are thus seldom seen in pure form. Vertebrobasilar ischemia manifests with various combinations of symptoms such as dizziness, usually vertigo, diplopia, facial weakness, ataxia and long tract signs.

A basilar artery occlusion produces massive deficits. One of these deficits is known as the "locked in state." In this condition, paralysis of the limbs and most of the bulbar muscle leaves the subject only able to communicate by moving the eyes or eyelids in a type of code. Occlusion of the basilar apex or top of the basilar is usually caused by emboli that lodge at the junction between the basilar artery and the two posterior cerebral arteries. The condition produces an initial reduction in arousal followed by blindness and amnesia due to an interruption of flow into the posterior cerebral arteries as well as abnormalities of vertical gaze and pupillary reactivity due to tegmental damage.

Venous occlusion can cause massive damage and death. This disease is less common than arterial cerebral vascular disease. As with ischemic stroke from arterial disease, the primary mechanism of brain damage is the reduction in capillary blood flow, in this instance because of increased outflow resistance from the blocked veins. Back transmission of high pressure into the capillary bed usually results in early brain swelling from edema and hemorrhagic infarction in subcortical white matter. The most dangerous form of venous disease arises when the superior sagittal sinus is occluded. Venous occlusion occurs in association with coagulation disorders, often in the purpural period, or in subjects with disseminated cancers or contagious diseases. If anticoagulant therapy is not initiated, superior sagittal sinus occlusion has a mortality rate of 25–40%.

Brief diffuse cerebral ischemia can cause syncope without any permanent sequelae. Prolonged diffuse ischemia in other organs has devastating consequences. The most common cause is a cardiac asystole or other cardiopulmonary failures, including infarction. Aortic dissection and global hypoxia or carbon monoxide poisoning can cause similar pictures. Diffuse hypoxia/ischemia typically kills neurons in the hippocampus, cerebellar Purkinje cells, striatum or cortical layers. Clinically, such a diffuse hypoxia/ischemia results in unconsciousness and in coma, followed in many instances by a chronic vegetative state. If the subject does not regain consciousness within a few days, the prognosis for the return of independent brain functions becomes very poor.

Hyperviscosity syndrome is another disease related to blood flow and ischemia. Cerebral blood flow is inversely related to blood viscosity. The latter is directly proportional to the number of circulating red and white cells, the aggregation state, the number of platelets and the plasma protein concentration. Blood flow is inversely proportional to the deformability of erythrocytes and blood velocity (shear rate). Subjects with hyperviscosity syndrome can present either with focal neurologic dysfunction or with diffuse or multifocus signs or symptoms including headache, visual disturbances, cognitive impairments or seizures.

There are a number of substances involved in clot formation and lysis. Plasminogen, also known as gluplasminogen, and plasmin are two of the primary substances involved in lysis.

Plasminogen is a protein, composed of 791 amino acids, that circulates in human plasma at a concentration of about 200 µg/ml. Plasminogen is the zymogen form of the fibrinolytic enzyme, plasmin, which has broad substrate specificity and is ultimately responsible for degrading blood clots. For the most part, fibrin proteolysis is mediated by the generation of plasmin within a fibrin clot from the plasminogen trapped within the clot. Fredenburgh & Nesheim, *J. Biol. Chem.* 267: 26150–56 (1992).

Plasminogen has five kringle domains within its amino-terminal heavy chain region that exhibit lysine-binding sites for recognition of lysine residues in fibrin. Plasminogen-plasmin conversion, both within a clot and at its surface, is facilitated by the affinity of tissue plasminogen activator ("t-PA") for fibrin, which results in a fibrin-dependent t-PA-induced plasminogen activation. Fredenburgh, loc. cit.

Once initiated, fibrinolysis results in several positive feedback reactions. For instance, plasmin-catalyzed cleavage of fibrin generates carboxy-terminal lysine residues, which in turn provide additional binding sites for both t-PA and plasminogen. This also facilitates plasmin-catalyzed conversion of glu-plasminogen to lys-plasminogen by a specific cleavage, which is a pre-activation step. Shih & Hajjar, *P.S.E.B.M.* 202: 258–64 (1993). In the literature, the term "lys-plasminogen" refers to forms of plasminogen where the N-terminal amino acid is lysine, valine or methionine. Nieuwenhuizen et al., *Eur. J. Biochem.* 174: 163–69 (1988). The conversion activity reflects a positive feedback reaction, because lys-plasminogen is a considerably better substrate than glu-plasminogen for both t-PA and urokinase, which may be caused by the enhanced affinity of lys-plasminogen for fibrin. The ratio of the Kcat/Km for t-PA-catalyzed activation of lys-plasminogen exceeds that of glu-plasminogen by about a factor of ten. Fredenburgh, loc. cit.

Fibrinolysis has been previously shown to be accelerated by the addition of lys-plasminogen in vivo and in vitro. In addition, when the use of exogenous lys-plasminogen was compared to the use of exogenous glu-plasminogen in similar experiments, 0.08 µmol lys-plasminogen produced the same degree of enhanced fibrinolysis as 0.67 µmol glu-plasminogen. Therefore, while both forms of plasminogen shorten the time for fibrinolysis, lys-plasminogen is about eight times more potent in this regard than glu-plasminogen. See Fredenburgh, supra.

Previous studies of lys-plasminogen have not implicated this protein for use in treatment of reperfusion injury. The conventional treatment for reperfusion injury is Flunarizine, which is only effective when administered prophylactically.

SUMMARY OF THE INVENTION

It is therefore an object of the present invention to provide a method for treating reperfusion injury to tissue.

It is also an object of the present invention to provide a method for treating ischemia, infarction or brain edema.

It is also another object of the present invention to provide a method for improving the microcirculation.

It is yet another object of the present invention to provide a method for treating the reperfusion injury that follows ischemic events.

It is yet another object of the present invention to provide a method for treating the reperfusion injury that follows ischemic events by administering a pharmaceutical composition comprising plasmin or a plasmin-forming protein, including zymogens and pre-activated zymogens of plasmin.

It is still another object of the present invention to provide a method for treating ischemia and the attendant reperfusion injury resulting from events following ischemia by administering a pharmaceutical composition comprising a plasminogen activator and plasmin or a plasmin-forming protein, as described above.

In accordance with one aspect of the present invention, a method is provided for treating reperfusion injury that comprises administering to a subject a pharmaceutical preparation comprising plasmin or a plasmin-forming protein and a pharmaceutically acceptable carrier. In a preferred embodiment, lys-plasminogen or related compounds are employed. The composition for use in this method may further comprise plasminogen activators such as tissue-type plasminogen activator, urokinase-type activators, pro-urokinase, streptokinase-type activators and plasmin.

Other objects, features and advantages of the present invention will become apparent from the following description and figures.

BRIEF DESCRIPTION OF THE FIGURES

FIG. 1 sets forth the scoring system used for evaluation of neurologic defects.

FIG. 2 is a summary of experimental data employing a rat model for evaluating the therapeutic benefits of lys-plasminogen as compared to a control.

"A" is rats with surgically-induced ischemia receiving 500 U/kg lys-plasminogen i.v. with blood reperfusion; "B" is rats with surgically-induced ischemia receiving 1.0 ml/kg isotonic saline i.v. with blood reperfusion; and "C" is rats having undergone a sham operation receiving 1.0 ml/kg isotonic saline i.v. ($\Delta$AB $p<0.001$; $\Delta$BC: $p<0.001$; $\Delta$AC: $p<0.05$).

Figure 3:
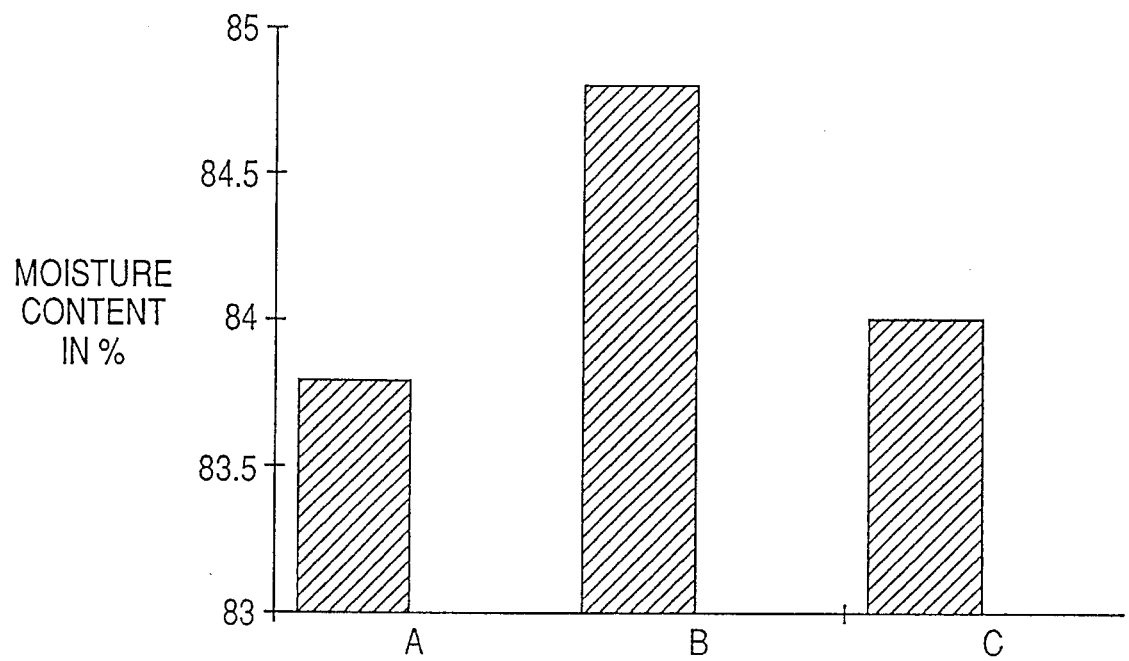
FIG. 3 is a graphic representation of the data from a controlled experiment evaluating the effect lys-plasminogen on the brain moisture content (edema) of rats with induced ischemia.
Figure 4:
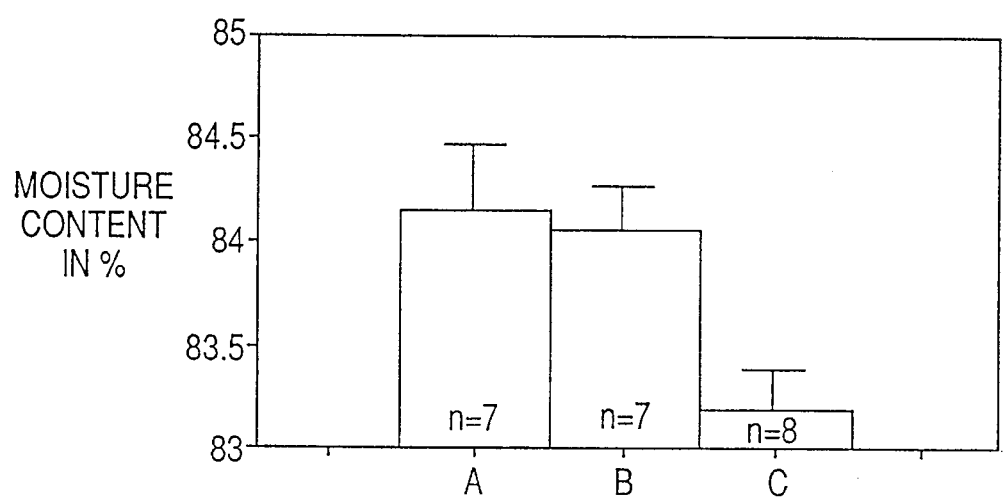

FIG. 4 is a graphic representation of the data from an experiment evaluating the effect of buffer on the brain moisture content (edema) of rats with induced ischemia, which serves as an additional control of the experiment of FIG. 3.

"A" is rats with surgically-induced ischemia receiving 1.0 ml/kg buffer i.v. with blood reperfusion (n=7); "B" is rats with surgically-induced ischemia receiving 1.0 ml/kg isotonic saline i.v. with blood reperfusion (n=7); and "C" is rats having undergone a sham operation receiving 1.0 ml/kg isotonic saline i.v. (n=8). ($\Delta$AB n.s.; $\Delta$BC: $p<0.01$; $\Delta$AC: $p<0.01$).

Figure 5:
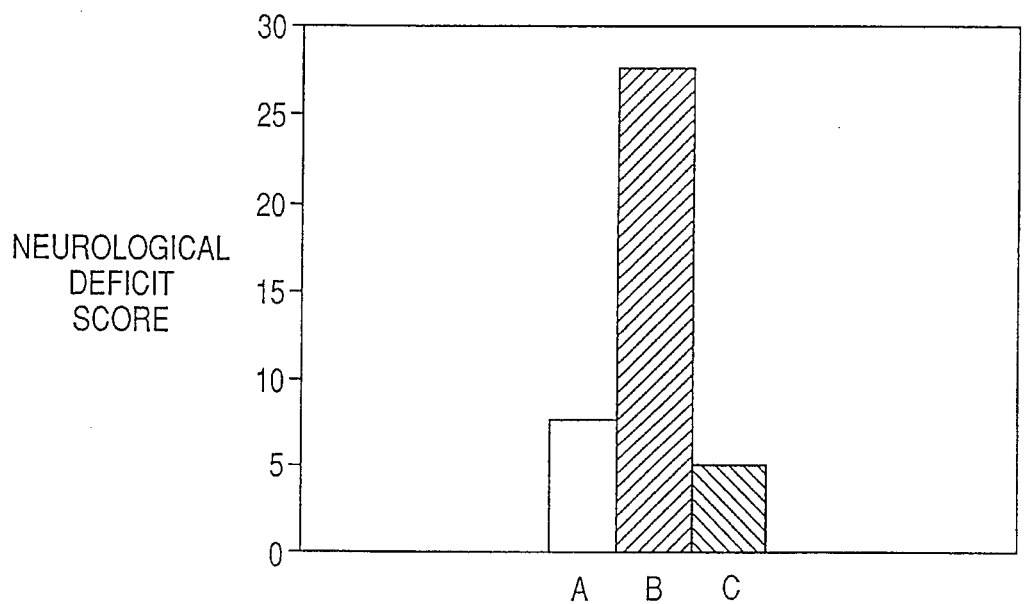

FIG. 5 is a graphic representation of the data from a controlled experiment evaluating the effect lys-plasminogen on the neurologic deficits of rats with induced ischemia.

The total score is based on individual ratings for state of consciousness, gait, muscle tone and performance (mean of 3 days per animal). The maximum score is 54 (n=10 per group). "A" is rats with surgically-induced ischemia receiving 500 U/kg/1.0 ml lys-plasminogen i.v. with blood reperfusion; "B" is rats with surgically-induced ischemia receiving 1.0 ml/kg isotonic saline i.v. with blood reperfusion; and "C" is rats having undergone a sham operation receiving 1.0 ml/kg isotonic saline i.v. ($\Delta$AB: $p<0.001$; $\Delta$BC: $p<0.001$; $\Delta$AC: $p=0.05$).

Figure 6:
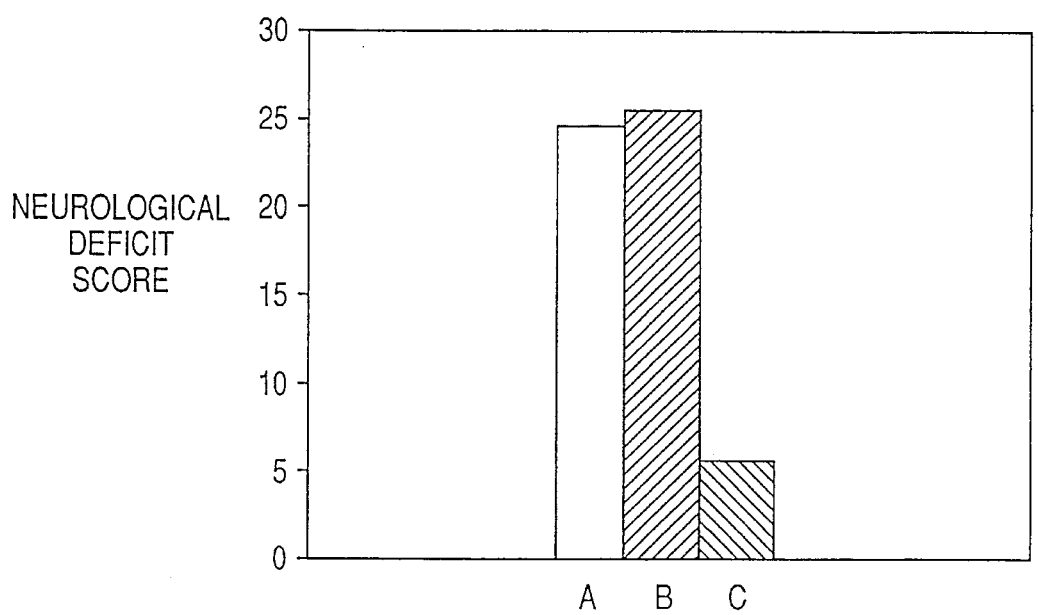

FIG. 6 is a graphic representation of the data from an experiment evaluating the effect of buffer on the neurologic deficits of rats with induced ischemia, which serves as an additional control of the experiment of FIG. 5.

The total score is based on individual ratings for state of consciousness, gait, muscle tone and performance (mean off 3 days per animal). The maximum score is 54 (n=6 per group). "A" is rats with surgically-induced ischemia receiving 1.0 ml/kg1.0 ml buffer i.v. with blood reperfusion; "B" is rats with surgically-induced ischemia receiving 1.0 ml/kg isotonic saline i.v. with blood reperfusion; and "C" is rats having undergone a sham operation receiving 1.0 ml/kg isotonic saline i.v. ($\Delta$AB: n.s; $\Delta$BC: $p<0.01$; $\Delta$AC: $p<0.01$).

DETAILED DESCRIPTION OF PREFERRED EMBODIMENTS

The present invention enables treatment of ischemic events, including cerebral ischemia, and reperfusion injury associated with ischemic events. Additionally, the present invention permits the treatment of ischemic events in a manner that avoids or minimizes the adverse effects associated with conventional treatments, such as reperfusion injury. The term "treatment" in its various grammatical forms refers to preventing, alleviating, minimizing or curing maladies or other adverse conditions.

It has been discovered that plasmin and plasmin-forming proteins, a category that includes lys-plasminogen, a pre-activated zymogen of plasmin, can be used, in accordance with the present invention, to attenuate or avoid reperfusion injury following an ischemic event. This beneficial effect can be obtained even when reperfusion already has started.

Lys-plasminogen itself can be employed as a treatment. All forms of lys-plasminogen are considered suitable for use with this invention as long as they retain the ability to affect the benefits described above. Also suitable for use pursuant to the present invention are fragments of lys-plasminogen and variants of lys-plasminogen, such as analogs, derivatives, muteins and mimetics of the natural molecule, that retain the ability to affect the benefits described above.

Fragments of lys-plasminogen refers to portions of the amino acid sequence of the lys-plasminogen polypeptide. These fragments can be generated directly from lys-plasminogen itself by chemical cleavage, by proteolytic enzyme digestion, or by combinations thereof. Additionally, such fragments can be created by recombinant techniques employing genomic or cDNA cloning methods. Furthermore, methods of synthesizing polypeptides directly from amino acid residues also exist. The variants of lys-plasminogen can be produced by these and other methods. Site-specific and region-directed mutagenesis techniques can be employed. See CURRENT PROTOCOLS IN MOLECULAR BIOLOGY vol. 1, ch. 8 (Ausubel et al. eds., J. Wiley & Sons 1989 & Supp. 1990–93); PROTEIN ENGINEERING (Oxender & Fox eds., A. Liss, Inc. 1987). In addition, linker-scanning and PCR-mediated techniques can be employed for mutagenesis. See PCR TECHNOLOGY (Erlich ed., Stockton Press 1989); CURRENT PROTOCOLS IN MOLECULAR BIOLOGY, vols. 1 & 2, supra. Non-peptide compounds that mimic the binding and function of a peptide ("mimetics") can be produced by the approach outlined in Saragovi et al., Science 253:792–95 (1991). Protein sequencing, structure and modeling approaches for use with any of the above techniques are disclosed in PROTEIN ENGINEERING, loc. cit. and CURRENT PROTOCOLS IN MOLECULAR BIOLOGY, vols. 1 & 2, supra.

Once a desired fragment or variant of lys-plasminogen is obtained, techniques described herein can be employed for determining whether the fragment or variant is effective for the above therapies, such as treatment of reperfusion injury and, if so, identifying an appropriate dosage range. The rat stroke model described in the example below is a simple and cost-efficient way of performing this testing in vivo.

The present invention also contemplates the use of progenitors of lys-plasminogen, that is, precursors of lys-plasminogen as well as substances that act on a lys-plasminogen precursor to generate lys-plasminogen. Illustrative of lys-plasminogen progenitors is glu-plasminogen, which is cleaved by an appropriate protease to generate lys-plasminogen. A substance effecting such a proteolytic cleavage is plasmin, the use of which falls within the scope of this invention as stated above. These rat stroke model described below is also useful for evaluating the effectiveness of lys-plasminogen progenitors.

Lys-plasminogen can be obtained by proteolytic cleavage of glu-plasminogen to remove amino acid sequences from glu-plasminogen. Methods of producing lys-plasminogen are described in greater detail in European Application 0 353 218. See also Neuwenhuizen, supra.

An example presented below demonstrates a previously unknown effect of lys-plasminogen which implicates its efficacy, and that of the lys-plasminogen variants and progenitors as well as plasmin and plasmin-forming proteins, in the treatment of reperfusion injury. Until now, lys-plasminogen was only known to function in fibrinolysis. It was not expected that plasmin or any plasmin-forming protein, such as lys-plasminogen, would be able to overcome the blood-brain barrier, which has been presumed to be necessary to be effective at the site of a cerebral ischemic event.

Other uses for lys-plasminogen exist as well. Lys-plasminogen is helpful in treating subjects after cardiac arrest. Lys-plasminogen administration may prevent the ischemic damage to neural cells. Lys-plasminogen can also be used in the treatment of total body ischemia (shock), ischemia of the bowels and lower extremities and for the preservation of organs for transplant by preventing ischemia.

Administration methods include those used for clotlysis treatments, typically intravenous routes. The dosage of Lys-plasminogen to be employed with this invention should be based on the weight of the subject and administered at a dosage of about 10 to 1000 caseinolytic units ("CU")/kg. Preferably, the dosage should be about 100 to 600 CU/kg, and more preferably the dosage should be about 500 CU/kg. The lys-plasminogen can be administered during blood reperfusion, which would occur when lys-plasminogen is administered along with conventional clot lysis treatments such as t-pa. Additionally, the beneficial effect of the lys-plasminogen can still be obtained when it is administered after reperfusion has already begun. Preferably, the lys-plasminogen should be administered before or within about 30 minutes after reperfusion has begun. Lys-plasminogen variants and progenitors should be administered in dosages that yield the same effect as the dosage ranges discussed above.

A treatment in accordance with the present invention can be effected advantageously via administration of the above-described substances in the form of injectable compositions. A typical composition for such purpose comprises a pharmaceutically acceptable carrier. An exemplary composition in this context is a lys-plasminogen buffer vehicle (9 g/L NaCl, 1 g/l $Na_3$ citrate •$2H_2O$, 3 g/l L-lysine, 6 g/l $NaH_2PO_4$•$2H_2O$ and 40,000 KIU/l aprotonin). Pharmaceutically acceptable carriers in this context include other aqueous solutions, non-toxic excipients, including salts, preservatives, buffers and the like, as described in REMINGTON'S PHARMACEUTICAL SCIENCES, 15th Ed. Easton: Mack Publishing Co. pp 1405–1412 and 1461–1487 (1975) and in THE NATIONAL FORMULARY XIV., 14th Ed. Washington: American Pharmaceutical Association (1975), the contents of which are hereby incorporated by reference. Examples of non-aqueous solvents are propylene glycol, polyethylene glycol, vegetable oil and injectable organic esters such as ethyloleate. Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobials, anti-oxidants, chelating agents and inert gases. The pH and exact concentration of the various components of the binding composition are adjusted according to routine skills in the art. See GOODMAN AND GILMAN'S THE PHARMACOLOGICAL BASIS FOR THERAPEUTICS (7th ed.).

EXAMPLE

Effect of Lys-Plasminogen on the Sequelae of Cerebral Ischemia in Rats

In this experimental series,-the effects of lys-plasminogen on the sequelae of experimentally induced ischemia in rats was evaluated. Two different approaches were employed to assess the neurologic consequences of ischemia. Ischemia was induced in rats as described below.

First, male Sprague-Dawley rats (weight 300–400 g) are anesthetized with 350 mg/kg choral hydrate i.p., and a catheter was then inserted into the jugular vein. Five milliliters of blood was withdrawn through the jugular catheter (100 IU heparin in the syringe) in order to reduce mean arterial blood pressure to 50 mm Hg. The prepared carotid arteries are exposed and clamped simultaneously with the blood withdrawal. The clamps are removed after a period of 30 minutes, and the withdrawn blood is reinfused (reperfusion). Fibrin sealant (Tisseel®) is applied to the wounds. The animals remain under anesthesia for a total of 24 hours (23.5 hours after reperfusion). After regaining consciousness, each animal undergoes one of the following procedures:

Assessment of brain edema:

Animals are maintained at constant body temperatures for a total of 24 hours, sacrificed with ether and the brains removed. Assessment of brain edema was performed using modifications of methods published for other species. Oh & Betz, Stroke 22: 915–21 (1991).

Moisture content, which is an excellent parameter for assessing ischemia/reperfusion-induced edema of the brain, is determined as follows: Both hemispheres are weighed, dried for 17 hours at 200° C., and reweighed. Moisture content is was calculated in percent of total moist weight according to the following formula:

$$\frac{\text{Moist weight} - \text{Dry weight}}{\text{Moist weight}} \times 100$$

Assessment of neurologic deficits:

Animals were assessed for neurologic deficits on the first, second and third post-operative days. Wauquier et al., *Neuropharmacology* 28: 837–46 (1989). State of consciousness, gait, muscle tone, performance on an overhead ladder tilted at 45°, and performance on a vertically mounted rotating disk were evaluated on the basis of the scoring system shown in FIG. 1. A cumulative score for the three days is calculated (maximum score=54).

Lys-plasminogen (IMMUNO AG) was administered intravenously by means of catheter into either the jugular or tail vein. These administrations were performed in increasing concentrations at various time points. Ischemic animals treated with isotonic saline served as positive controls, while animals subjected to a sham operation and treated with isotonic saline served as negative controls.

The above-described lys-plasminogen buffer was tested using each of these procedures in separate experiments. A summary of dosage, administration schedule, experimental procedures and results is set forth in FIG. 2.

The results for 500 CU/kg lys-plasminogen (and the buffer employed as a control) are shown in FIGS. 3 and 4 for edema and FIGS. 5 and 6 for neurologic deficits. Significance values were based on t-tests for edema and the Kruskal-Wallis test assuming a chi-square distribution for neurologic deficits.

A dose of 500 CU/kg of lys-plasminogen showed a significant protective effect on the sequence of experimentally induced cerebral ischemia in rats. The schedule of administration did not play an essential role. Notably, the lys-plasminogen still exerted a protective effect even when it was administered 30 minutes after the beginning of reperfusion. This contrasts with results obtained for the standard therapeutic measure flunarizine, which is a calcium antagonist used in clinical practice. Flunarizine (0.63 mg/kg given intravenously) was effective when administered in the reperfused blood, but had no effect when administered 30 minutes after reperfusion (data not shown).

Lys-plasminogen (500 CU/kg) was capable of reversing the effects of cerebral ischemia as assessed on the basis of brain edema and neurologic deficits in a rat model of experimental ischemia. The buffer used in the lys-plasminogen preparation had no effect. In contrast to a standard therapeutic measure (flunarizine), lys-plasminogen was effective even when administered 30 minutes after reperfusion.

It is to be understood that the description, figures and specific examples, while indicating preferred embodiments of the invention are given by way of illustration and are not intended to limit the present invention. Various changes and modifications within the spirit and scope of the invention will become apparent to those skilled in the art from the discussion and disclosure contained herein.

What is claimed is:

1. A method of treating reperfusion injury, comprising the step of administering to a subject in need thereof a pharmaceutical preparation comprising lys-plasminogen in a dosage of about 10 to 1000 CU of lys-plasminogen per kg of said subject.

2. The method according to claim 1, wherein said pharmaceutical composition is administered in a dosage of about 100 to 600 CU of lys-plasminogen per kg of said subject.

3. The method according to claim 2, wherein said pharmaceutical composition is administered in a dosage of about 500 CU of lys-plasminogen per kg of said subject.

4. The method according to claim 1, wherein said lys-plasminogen is administered before or within about 30 minutes after reperfusion has begun.

5. The method according to claim 1, wherein said lys-plasminogen has been treated to inactivate viruses prior to administration.

6. A method of treating brain edema, comprising the step of administering to a subject having brain edema a pharmaceutical composition comprising lys-plasminogen in an amount sufficient to provide a lessening of brain edema caused by cerebral ischemia.

7. The method according to claim 6, wherein said lys-plasminogen has been treated to inactivate viruses prior to administration.

8. A method of treating reperfusion injury in a subject, comprising the step of administering to said subject a pharmaceutical composition consisting essentially of lys-plasminogen in an amount sufficient to provide a protective effect from reperfusion injury.

9. The method according to claim 8, wherein said lys-plasminogen has been treated to inactivate viruses prior to administration.

* * * * *